United States Patent
Criswell et al.

(10) Patent No.: US 11,373,248 B1
(45) Date of Patent: Jun. 28, 2022

(54) METHOD AND APPARATUS FOR RISK ADJUSTMENT

(71) Applicant: Pulse8, Inc., Annapolis, MD (US)

(72) Inventors: John Criswell, Annapolis, MD (US); Victor Caro, Snoqualmie, WA (US); Scott Stratton, Orange, CT (US); Paul Schiele, Collegeville, PA (US)

(73) Assignee: Pulse8, Inc., Annapolis, MD (US)

( * ) Notice: Subject to any disclaimer, the term of this patent is extended or adjusted under 35 U.S.C. 154(b) by 698 days.

(21) Appl. No.: 15/975,326

(22) Filed: May 9, 2018

Related U.S. Application Data

(60) Provisional application No. 62/503,423, filed on May 9, 2017.

(51) Int. Cl.
| | | |
|---|---|---|
| *G06Q 40/08* | (2012.01) | |
| *G16H 50/30* | (2018.01) | |
| *G16H 10/60* | (2018.01) | |
| *G16H 40/20* | (2018.01) | |

(52) U.S. Cl.
CPC .............. *G06Q 40/08* (2013.01); *G16H 10/60* (2018.01); *G16H 50/30* (2018.01); *G16H 40/20* (2018.01)

(58) Field of Classification Search
CPC ........ G06Q 10/06; G06Q 40/04; G06Q 40/08; G06Q 50/06; G06Q 10/047; G06Q 20/10; G06Q 40/06; G06Q 50/30; G06Q 40/00; G06Q 10/04; G06Q 10/06395; G06Q 10/067; G06Q 10/1097; G06Q 30/016; G06Q 30/0611; G06Q 40/02; G06Q 40/025; G06Q 40/12; G06Q 50/01
See application file for complete search history.

(56) References Cited

U.S. PATENT DOCUMENTS

| | | | |
|---|---|---|---|
| 2003/0115195 A1* | 6/2003 | Fogel | G06Q 10/10 |
| 2011/0087500 A1* | 4/2011 | McCallum | G06Q 10/10 705/3 |
| 2014/0164019 A1* | 6/2014 | Thesman | G06Q 40/08 705/3 |

(Continued)

OTHER PUBLICATIONS

Rosenberg, et al ."Effect of Utilization Review in a fee-for-service Health insurance plan." 1995. The New England Journal of Medicine, vol. 333, No. 20; pp. 1326-1330 (Year: 1995).*

*Primary Examiner* — Rachel L. Porter
(74) *Attorney, Agent, or Firm* — Lerner, David, Littenberg, Krumholz & Mentlik, LLP

(57) ABSTRACT

The technology relates to determining service item management opportunities. One or more processors may receive a set of client data via communication network. The one or more processors may identify one or more service item management opportunities by determining service items in the set of client data which satisfy at least one or more rules and assign a confidence value to the one or more service item management opportunities. For each of the one or more service item management opportunities, a recommended intervention type based on the respective assigned confidence value may be determined and for each of the one or more service item management opportunities, a transmission may be caused by the one or more processors, via the communication network to an external device, of rendering information indicating the service item management opportunity and the recommended intervention type.

20 Claims, 7 Drawing Sheets

(56) References Cited

U.S. PATENT DOCUMENTS

| | | | |
|---|---|---|---|
| 2015/0261796 A1* | 9/2015 | Gould | G06F 16/215 707/694 |
| 2015/0317743 A1* | 11/2015 | Flam | G06F 19/00 705/4 |
| 2016/0196611 A1* | 7/2016 | Steele | G06Q 40/08 705/4 |
| 2017/0162069 A1* | 6/2017 | Petakov | G16H 20/60 |
| 2018/0046764 A1* | 2/2018 | Katwala | G16H 15/00 |
| 2020/0057612 A1* | 2/2020 | Doyle | G06F 8/35 |

* cited by examiner

METHOD AND APPARATUS FOR RISK ADJUSTMENT

CROSS-REFERENCE TO RELATED APPLICATIONS

The present application claims the benefit of the filing date of U.S. Provisional Patent Application No. 62/503,423 filed May 9, 2017, the disclosure of which is hereby incorporated herein by reference.

BACKGROUND

The healthcare industry's transition from paper to computer based record keeping has resulted in a proliferation of digital healthcare data. As the amount of healthcare data produced by the healthcare industry continues to increase, actionable information which may be used to improve the efficiency and effectiveness of healthcare may be culled from the healthcare data. However, recognizing this actionable information from the overwhelming amount of healthcare data becomes increasingly difficult as the actionable information may be based on unlinked data scattered across many different sources of information.

Accordingly, there is a need for systems, apparatuses, and methods which may provide the healthcare industry with the ability to efficiently identify actionable information to provide better service, more efficiently and cheaply.

SUMMARY

Embodiments within the disclosure relate generally to a risk adjustment system. One aspect includes a computer implemented method for determining service item management opportunities. The method may include receiving, at one or more processors, via a communication network, a set of client data and identifying one or more service item management opportunities, with the one or more processors, by determining service items in the set of client data which satisfy at least one or more rules. The one or more processors may assign a confidence value to the one or more service item management opportunities and determine, for each of the one or more service item management opportunities, a recommended intervention type based on the respective assigned confidence value. The one or more processors may cause, for each of the one or more service item management opportunities, via the communication network to an external device, of rendering information indicating the service item management opportunity and the recommended intervention type.

In some embodiments, identifying the one or more service item management opportunities may further include identifying, for each item in the set of client data, a set of rules from the one or more rules, determining for each item, at least one validation test, based on the respective set one or more rules, and performing, for each item, each respective determined validation test to determine whether the item satisfies at least one of the set of rules.

In some embodiments, assigning the confidence value to the one or more service item management opportunities may further include, for each item in the set of client data determining a classification, identifying related items from the set of client data based on the classification and increasing the confidence value for each item based on each identified related item.

In some embodiments, each of the one or more service item management opportunities are assigned a risk adjustment factor (RAF), and wherein the risk adjustment factor represents an opportunity score corresponding to a condition in which the one or more service item management opportunity is confirmed.

In some embodiments, the RAF is normalized.

In some embodiments, the transmission causes a visual or audio alert to be automatically generated at the external device.

BRIEF DESCRIPTION OF THE DRAWINGS

The foregoing aspects, features and advantages of the present invention will be further appreciated when considered with reference to the following description of exemplary embodiments and accompanying drawings, wherein like reference numerals represent like elements. In describing the exemplary embodiments of the invention illustrated in the drawings, specific terminology may be used for the sake of clarity. However, the aspects of the invention are not intended to be limited to the specific terms used.

DETAILED DESCRIPTION

Overview

Figure 1:
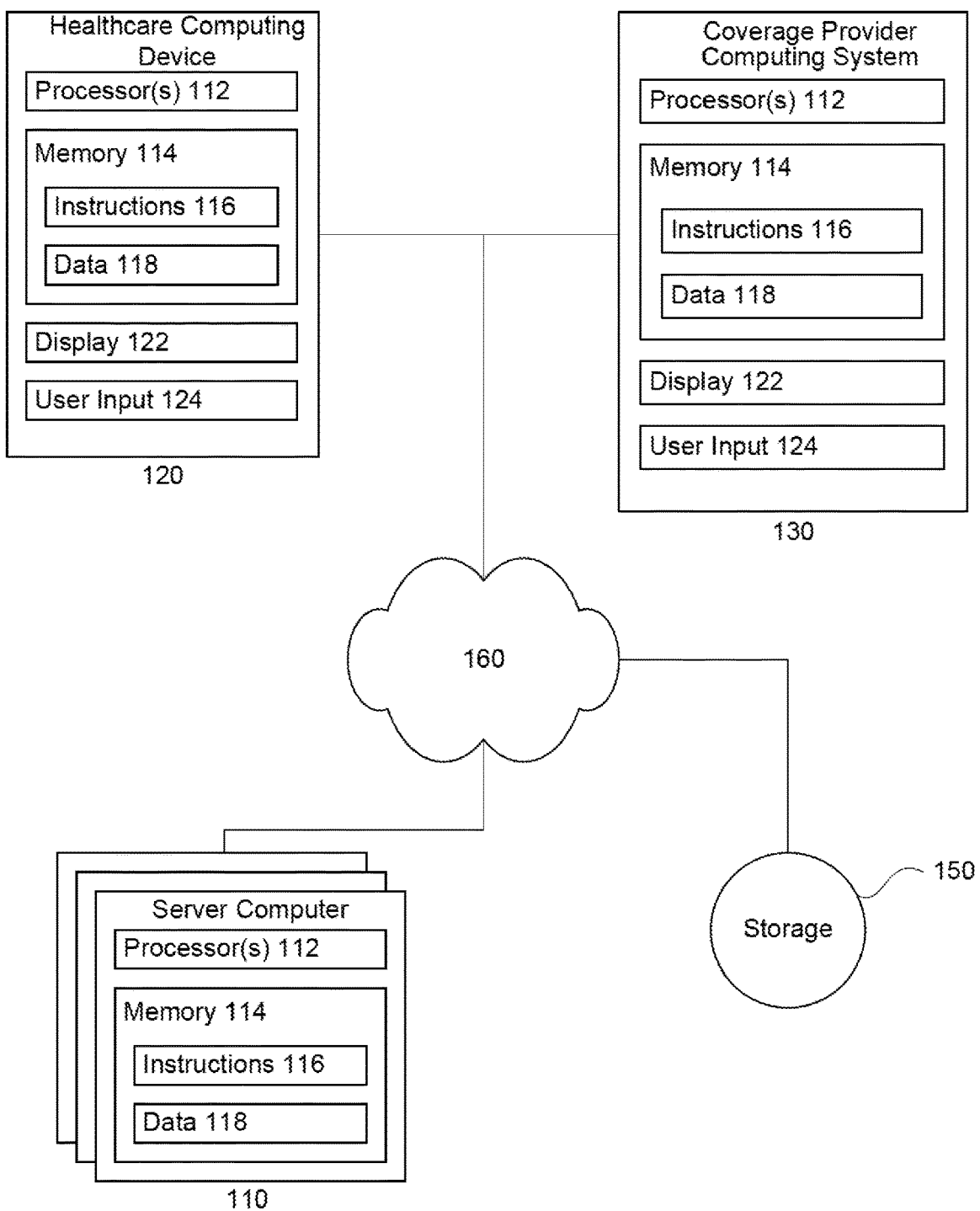
FIG. 1 is a functional diagram of an example system in accordance with aspects of the disclosure.

The technology of the disclosure relates to, by way of example, identification, prioritization, resolution, and efficacy evaluation of opportunities in the documentation of service items, such as medical care and coverage. In addition, the technology may assist in resolving the opportunities to help care providers and coverage providers adjust their risk, assure quality service, assure quality care, and avoid waste and billing errors.

Coverage providers, such as health insurance providers and other entities, such as provider-sponsored plans or Accountable Care Organizations which comprise providers sharing risk with one or more health plans, operate under the regulations of many government programs, such as the Affordable Care Act (ACA), Medicare Advantage (MA), and Managed Medicaid (MM). Coverage providers which operate within the confines of such programs may earn additional revenues by documenting that their respective clients (i.e., patients) require more care than other coverage provider's clients. In other words, coverage providers which take on "sicker" clients may receive more money from the government programs to cover their clients' services. This allocation of funds between coverage providers based on the documented risk of each coverage provider's clients is called risk adjustment.

Coverage providers may maximize their risk adjustment, thereby maximizing compensation from the government programs, by reporting every risk adjusting condition their clients suffer from to increase their respective risk scores. In this regard, certain conditions, such as hypertension, will have no effect on a health insurance provider's risk score, while other conditions, such as type II diabetes will. The conditions which do and do not affect a coverage provider's risk score may differ between government programs.

To assure the coverage providers do not inflate their risk score, the government programs may audit the claims submitted by the coverage providers. The audits may check the claims for accuracy by determining whether the client of the coverage provider for which a claim is entered is eligible for the service approved and paid by the plan, and whether the health care provider of the service (e.g., doctor, nurse, vendor, etc.) is eligible to supply the service. Additionally the government program may check the accuracy of the claim to assure it is valid by, for example, comparing diagnosis codes, procedure codes, and other such codes against documented evidence in the client's medical records, that the condition was properly diagnosed and subsequently treated per accepted medical standards. Substantial penalties, such as fines and lower payments may result if a coverage provider submits an invalid claim.

The features described herein enable coverage providers to maximize their risk adjustment. For instance, the documentation of service items for the health care provided to a client may be generated by coverage providers and health care providers, amongst other individuals and businesses. This documentation may be reviewed in view of the client's past service item documentation, as well as in view of other sources of information, such as the client's medical and pharmacy claims, lab results, care management data, health risk assessments, medical records, and other such sources of information. In this regard, some or all of the data within the service item documentation and other sources of information may be applied against one or more rules to determine if the information satisfies the one or more rules. Satisfaction of one or more of the rules would indicate a service item management opportunity for the coverage provider to identify a client's conditions which were previously unknown or not entered into the service item documentation. In other words, the review of the data may allow a coverage provider to determine service item management opportunities, such as whether the client has an unidentified condition and/or whether the condition has not been properly documented.

The features described herein may also allow for coverage providers to identify additional conditions of their clients, while assuring any submission of the additional conditions to a government agency will be verified by the government agency to which the submissions were submitted. For instance, coverage providers may be assured that submissions made to the government systems are (i) eligible for coverage at time of service; (ii) acceptable for risk-adjustment; and/or (iii) that the diagnoses within the submissions satisfy hierarchical condition categories (HCC) definitions. In addition, the identified conditions may be shared with the health care providers so that the clients of the coverage provider are treated or reviewed for the identified conditions. Accordingly, the systems, apparatuses, and methods described herein provide the healthcare industry with the ability to efficiently identify actionable information to provide better service, more efficiently and cheaply.

Example Systems

Figure 2:
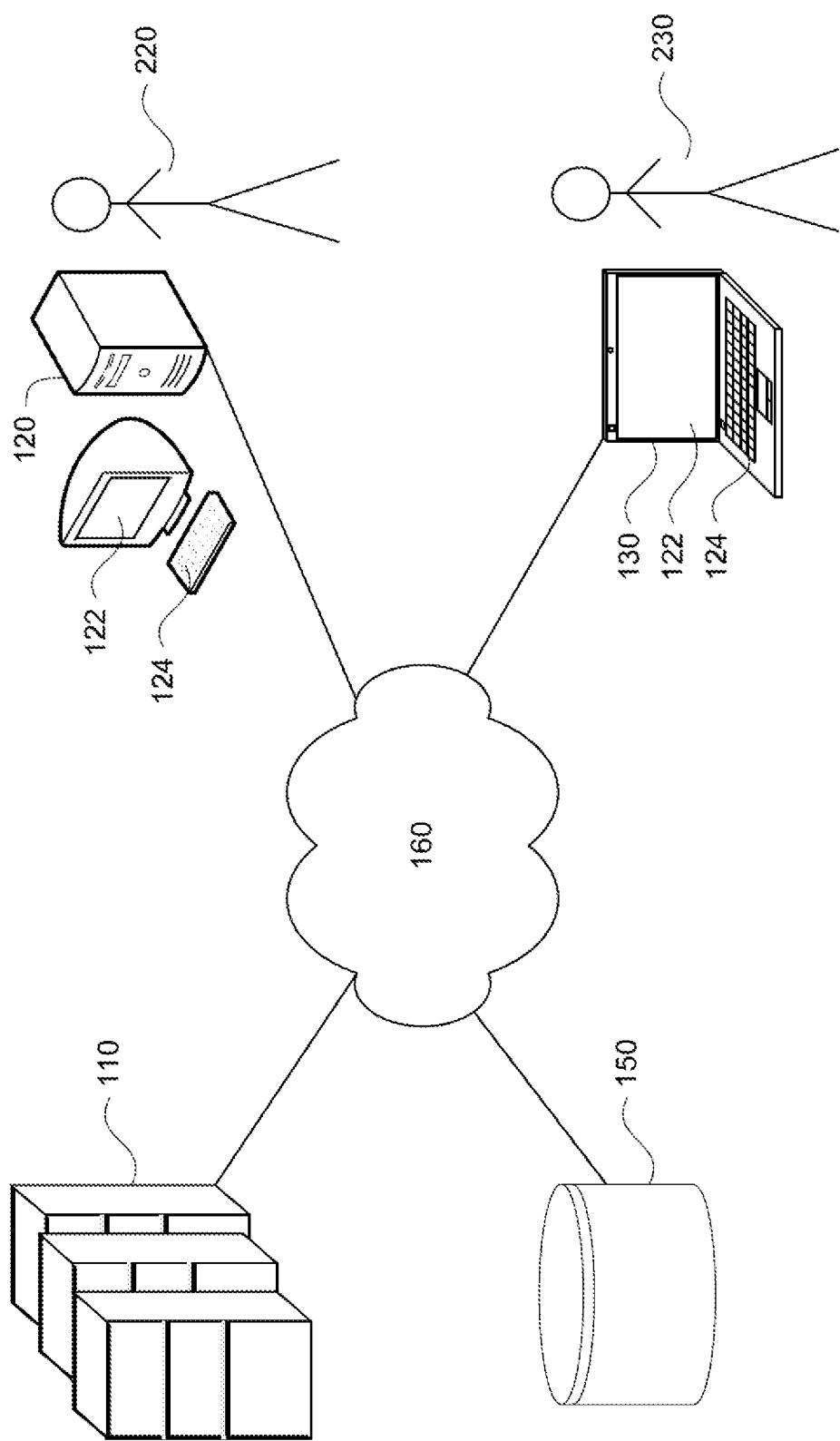
FIG. 2 is a pictorial diagram of the example system of FIG. 1.

FIGS. 1 and 2 illustrate an example system 100 in which the features described herein may be implemented. It should not be considered as limiting the scope of the disclosure or usefulness of the features described herein. In this example, system 100 may include computing devices 110-130, which include server computers 110, healthcare computing device 120, and coverage provider computing device 130, as well as storage system 150. Each computing device 110-130 may include one or more processors 112, one or more memory 114, and other components commonly found in computing devices.

Memory 114 of each of computing devices 110, 120, and 130 may store information accessible by the one or more processors 112, including instructions 116 that may be executed by the one or more processors 112. Memory may also include data 118 that can be stored, manipulated, or retrieved by the processor. Such data 118 may also be used for executing the instructions 116 and/or for performing other functions. Such memory may be any type of non-transitory media readable by the one or more processors, such as a hard-drive, solid state hard-drive, memory card, ROM, RAM, DVD, CD-ROM, write-capable, read-only memories, etc.

The instructions 116 may be any set of instructions capable of being read and executed by the one or more processors. The instructions may be stored in a location separate from the computing device, such as in a network attached storage drive such as storage system 150, or locally at the computing device. The terms "instructions," "functions," "application," "steps," and "programs" may be used interchangeably herein.

Data 118 may be stored, retrieved and/or modified by the one or more processors in accordance with the instructions 116. Such data may be stored in one or more formats or structures, such as in a relational or non-relational database, in a SQL database, as a table having many different fields and records, XLS, TXT, or XML documents. The data may also be formatted in any computing device-readable format. In some embodiments the data may be encrypted.

The one or more processors 112 may be any type of processor, or more than one type of processor. For example, the one or more processors 112 may be CPUs from Intel, AMD, and Apple, or application specific integrated circuits (ASIC) or system on chips (SoCs).

FIG. 1 illustrates the components of the computing devices 110 as being single components, however, the components may actually comprise multiple processors, computers, computing devices, or memories that may or may not be stored within the same physical housing. For example, the memory may be a hard drive or other storage media located in housings different from that of the computing devices 110. The same may be true of the components within the other computing devices 120 and 130. Accordingly, references to a processor, computer, computing device, or memory will be understood to include references to a collection of processors, computers, computing devices, or memories that may or may not operate in parallel. Further, although some functions described below are indicated as taking place on a single computing device having a single processor, various aspects of the subject matter described herein may be implemented by a plurality of computing devices in series or in parallel.

Storage device 150 may be of any type of storage capable of storing information accessible by the server computing devices 110, healthcare computing device 120, or coverage provider computing system 130, such as a hard-drive, a solid state hard drive, NAND memory, ROM, RAM, DVD, CD-ROM, write-capable, and read-only memories. In addition, storage device 150 may include a distributed storage device where data is stored on a plurality of different storage devices which may be physically located at the same or different geographic locations, such as network attached storage. Storage device 150 may be connected to the computing devices via the network 160 as shown in FIG. 1, and/or may be directly connected to any of the computing devices 110, 120, and 130.

The network 160 may include interconnected protocols and systems. For example, the network 160 may be implemented via the Internet, intranets, local area networks (LAN), wide area networks (WAN), etc. Communication protocols such as Ethernet, Wi-Fi, and HTTP, Bluetooth, LTE, 3G, 4G, Edge, etc., and various combinations of the foregoing may be used to allow the nodes to communicate.

Each of the computing devices 110, 120, and 130 may be implemented by directly and/or indirectly communicating over the network 160. In this regard, each of the computing devices 110, 120, and 130, as well as storage device 150, may be at different nodes of a network 160 and capable of directly and indirectly communicating with other nodes of network 160. As an example, each of the computing devices 110-130 may include web servers capable of communicating with storage system 150 via the network. For example, one or more server computing devices 110 may use network 160 to transmit and present information to a user, such as health care provider 220 or coverage provider 230, on a display, such as displays 122 of computing devices 120 and 130.

Although only a few computing devices are depicted in FIGS. 1-2, a system may include a large number of connected computing devices 110, 120, and 130, with each different computing device being at a different node of the network 160. For example, each coverage provider and health care provider may have at least one coverage provider computing device 130 and health care provider computing device, respectively.

Each of the server computing devices 110 may include web servers which are capable of communicating with storage system 150 as well as with computing devices 120 and 130 via the network. For example, one or more of server computing devices 110 may use network 160 to transmit and present information to a user, such as user 220 or 230, on a display, such as displays 122 of computing devices 120 or 130.

Each of the computing devices 120 and 130 may be configured similarly to the server computing devices 110, with one or more processors, memory and instructions as described above. Computing devices 120 and 130 may be a personal computing device intended for use by a user 220 and 230, and have all of the components normally used in connection with a personal computing device such as a central processing unit (CPU), memory (e.g., RAM and internal hard drives) storing data and instructions, a display such as displays 122, (e.g., a monitor having a screen, a touch-screen, a projector, a television, or other device that is operable to display information), and user input device 124 (e.g., a mouse, keyboard, touch-screen, or microphone). Although not shown, server computing devices 110 may also include displays and user input devices.

Although the computing devices 120 and 130 may each comprise a full-sized personal computing device, they may alternatively comprise mobile computing devices capable of wirelessly exchanging data with a server over a network such as the Internet. By way of example only, healthcare computing device 120, although depicted as a personal computing device, may be a mobile phone or a device such as a wireless-enabled PDA, a tablet PC, or a netbook that is capable of obtaining information via the Internet. In another example, coverage provider computing device 130 may be a laptop computer.

The healthcare computing device 120 may be configured to provide specific functions in accordance with embodiments of the technology. For example, the healthcare computing device 120 may be programmed to allow the healthcare provider to submit client data to a client's coverage provider or to an online database. Such client database may be structured or unstructured. Such client data may include data types commonly created during the administration of healthcare services, such as data found in Table 1, below, although such client data may be retrieved from other sources, such as external databases as well.

TABLE 1

Client Data

Medical Services as defined by Current Procedural Terminology (CPT) and Healthcare Common Procedure Coding System HCPCs (e.g., evaluation and management, consultations, interpretations, etc.)
Lab Tests Conducted and Lab Test Results/Values
Prescribed Drugs (i.e., drugs prescribed by a doctor for fulfillment at a retail outlet or via mail order, as well as those billed via HCPCs as medical services)
Medical Equipment
Medical Supplies
Surgical Procedures
Diagnostic and Therapeutic Procedures
Revenue and Accommodation Codes
Disease Registry Entries
Care Management Program Data (i.e., data from third party businesses who help clients manage their care, including high risk clients)
Consumer Behavior and Lifestyle Data (e.g., gym memberships, eating habits, etc.)
Unstructured or Semi-structured Client Information (e.g., medical charts and medical records which may be imaged and or converted to a machine readable format such as through optical character recognition (OCR))
Health Assessments Coverage provider computing device 130 may be configured to provide specific functions in accordance with embodiments of the technology. In some embodiments the coverage provider computing device may be programmed to store received client data in memory or storage device 150. Coverage provider computing device 130 may be further configured to communicate with server 110. The coverage provider computing device 130 may be able to perform all of the methods described herein, including all of the function of the server computing devices 110.

One or more servers, such as server computing devices 110 may be configured to provide specific functions in accordance with embodiments of the technology. In this regard, one or more servers may maintain one or more storage devices, such as storage device 150, on which client data as well as other additional data used to recognize and confirm service item management opportunities may be stored. Additionally, the one or more server computing devices 110 may be programmed with programs to perform some or all of the operations described herein.

The additional data which may be used to identify service item management opportunities may be stored in the storage device 150 in conjunction or association with the client data. Such additional data may include references and rules. References may be stored individually or in tables, and may include groupings of detailed codes, such national drug codes (NDC), metadata associated with the NDC, such as on and off label designations as well as therapeutic ranges of drugs, international code sets, such as logical observation identifiers names and codes (LOINC). In some embodiments, the one or more servers may access the additional data through external providers.

The rules may contain if-then-else type programming logic, or other conditional programming logic, which may enable the server computing devices 110 to analyze the additional data and client data to determine whether service item management opportunities are present. Rules may be added, adjusted, removed, or deactivated based on external and internal factors found within the data. For example, external factors which may include data external to client's data such as, by way of example, data indicating (i) changes to clinical thresholds and expected values (e.g., a shift in a normal range of a lab test); (ii) limited uses of a medication or approved new uses of a medication. Such limitations and uses may be defined by medical authorities, such as the FDA; (iii) new off-label (non-FDA approved) uses of a medicine; and (iv) odds of having a condition given various combinations of risk factors. Such odds may be provided by published research articles, press releases, etc.

Internal factors may include factors determined from within the client's data such as, by way of example (i) changes in odds of having a condition based on various predictor variables that may or may not be documented in published studies. Such changes may be determined based on data mining, Bayesian, or other multivariate analyses; (ii) analyses of "false-negatives" (i.e., confirmed conditions that were not previously defined as service item management opportunities). False-negatives may be identified by factors or interactions that would reduce this rate, such as looking at additional types of data previously neglected; (iii) analysis of likely "false-positives" (i.e., service item management opportunities identified by the rules, but which health care providers stated were not present). False-positives may be identifies by determining where the inference was made and identify factors or interactions that resulted in the improper inference. For example, a new off-label use of a drug may not have been taken into consideration, and as such, the new off-label use should be factored into the analysis; (iv) clinical reviews of all rules and their reliability may result in our manual adjustments made. For example, when subjective valuation is needed manual adjustments to the confidence in the result of a rule may be made.

Additionally, the rules may be associated with metadata which may include refinements to the programming logic that are particular to a type of data. In this regard, the metadata may define normal and abnormal values for certain rules. For example, an abnormal value may be defined as values within a range, outside a range, or above or below a reference value. In another example, the metadata may define normal values as data which contains a particular text string or sufficiently similar variant.

The metadata of the rules may be adjusted based on a continued review of the client data and additional data. In this regard, depending on the results of the rules, the abnormal finding may have to occur at least a threshold number of times within close proximity or must be spread out over a number of months or years.

The data described herein including the client data and metadata may be stored in compliance with handled in full compliance with all governmental regulations and obligations. For instance, storage of the data may be stored and retrieved in full compliance with the Health Insurance Portability and Accountability Act (HIPAA) and the HITECH Act. Further, the data may be password protected and stored behind one or more firewalls.

Example Methods

For purposes of illustrating the features of the present technology, exemplary processes for service item management opportunity identification as shown in FIGS. 3-7, are described below in connection with operations performed at components of the system 100, as described in FIGS. 1 and 2. It is to be understood that the some or all of the operations performed at the server computing devices 110 may be performed at the coverage provider computing device 130, and some or all of the operations performed at the healthcare computing device 120, and vice versa.

Figure 3:
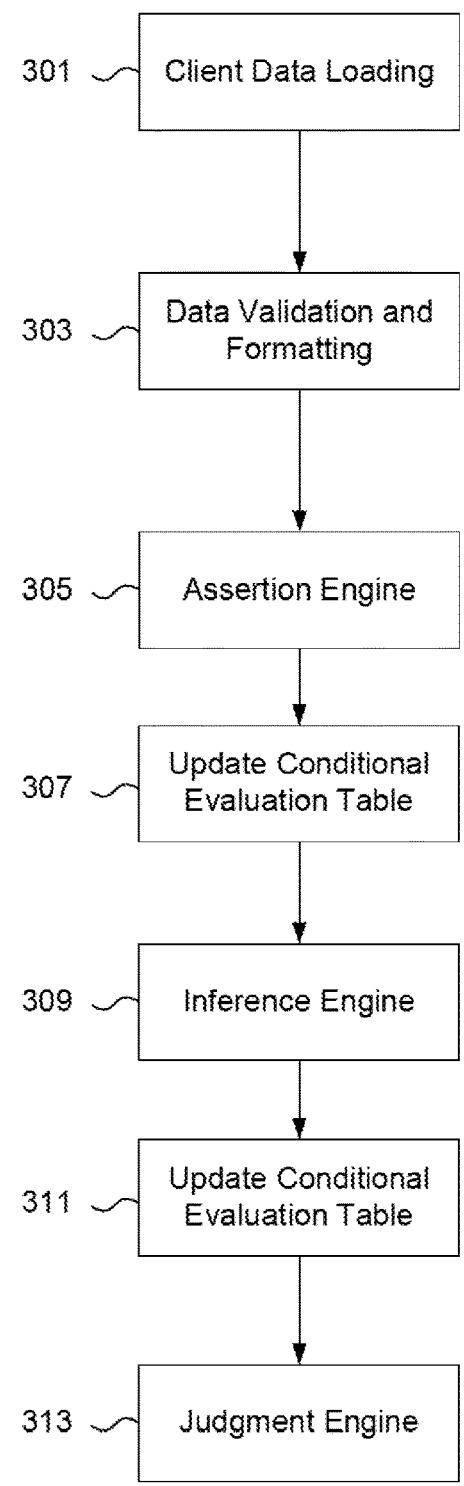
FIG. 3 is a flow diagram of identifying service item management opportunities in accordance with aspects of the disclosure.

Referring now to FIG. 3, a high-level block diagram 300 of service item management opportunity identification for risk adjustment is shown. In this regard, client data may be received and loaded by a server computing device, such as server computer 110, as shown in block 301. The client data may include one or more items of client data described in table 1 above. Each piece of client data may be associated with one or more clients of a coverage provider. In some embodiments the server computer 110 may transmit and/or receive data via secure file transfer protocol (sFTP).

Upon the client data being received and loaded, the server computing device, the data may be linked, validated, augmented, formatted, or otherwise managed, as shown in block 303. For instance, the client data may come from any number of sources, some of which may be third parties. As such, the client data may be validated to assure that the data received falls within expected value ranges or matches expected terms. For instance, client NDC code may be compared to a table of NDC codes to assure that the client NDC code is valid. In some embodiments, the client data may need to be formatted, such that the client data is converted from one format to another format which is usable by the various engines described herein.

Additionally, portions of the client data may contain multiple data items from the same client, but with no indication or association that the multiple data items belong to the same client. For instance, each client may have a unique identifier assigned by one or more health care providers and/or insurers so that the health care providers and insurers may track the client's data throughout their respective lifetimes. However, each client may be assigned a different identifier by each health care provider and/or insurer. As such, the client's data from each different identifier may be aggregated together based on a determination that the different identifier's identify the same client. For example, client data containing the same social security number or the same health history may indicate the same client and may be associated with that same client.

Client data may also be augmented with additional data. For example, a client's primary care practitioner (PCP) may be inferred from the client's data and assigned to the client. Such a determination may assist in pay for performance service management opportunity.

Once the client data is formatted, linked, augmented, and/or validated, the client data may be passed to an assertion engine and, subsequently, an inference engine, as shown in blocks 305 and 309. The assertion engine may run the client data through one or more rules developed or approved by healthcare experts to determine if the client data satisfies one or more rules. The inference engine may then employ predetermined predictive models that process complex nuances and interactions among the client data to determine if service item management opportunities exist based the results of the assertion engine.

Both the assertion engine and the inference engine may update a conditional evaluation table. For instance, the assertion engine, upon determining a portion of the client data satisfies a rule, may write a record into a condition evaluation table with identifiers for the client, the source transaction (i.e., a claim identification (ID) indicating association of the client data with a particular client), a condition detected, a value found, and a confidence rating of the condition detected, etc. as shown in block 307. In another example, the inference engine may output a strength rating for an identified opportunity (i.e., the condition detected) to the conditional evaluation table as shown in block 311.

The evaluations by the assertion and inference engines may be specific to a particular year. In this regard, opportunities for risk adjustment may be limited to a one year period or more or less. Moreover, some client conditions may part of a condition hierarchy (i.e., a set of conditions ordered by severity, such as diabetes, or disease progression, such as cancer,) of which only a single condition may be pursued as a service item management opportunity. The assertion and inference engines may generate factors comprising a determination of whether any of the two or more conditions surpass a threshold to become a service item management opportunity, how many within the hierarchy exceed it, along with a composite determination of overall probability that each opportunity is real (e.g., determine a confidence rating for each identified service item management opportunity.)

A judgment engine may evaluate the factors, as shown in block 313. In this regard, the judgment engine may evaluate the identified opportunity and provide a risk adjustment factor to determine an anticipated financial impact the identified opportunity may have on the coverage provider. The coverage provider may then determine whether or not to pursue the identified opportunity.

Figure 4:
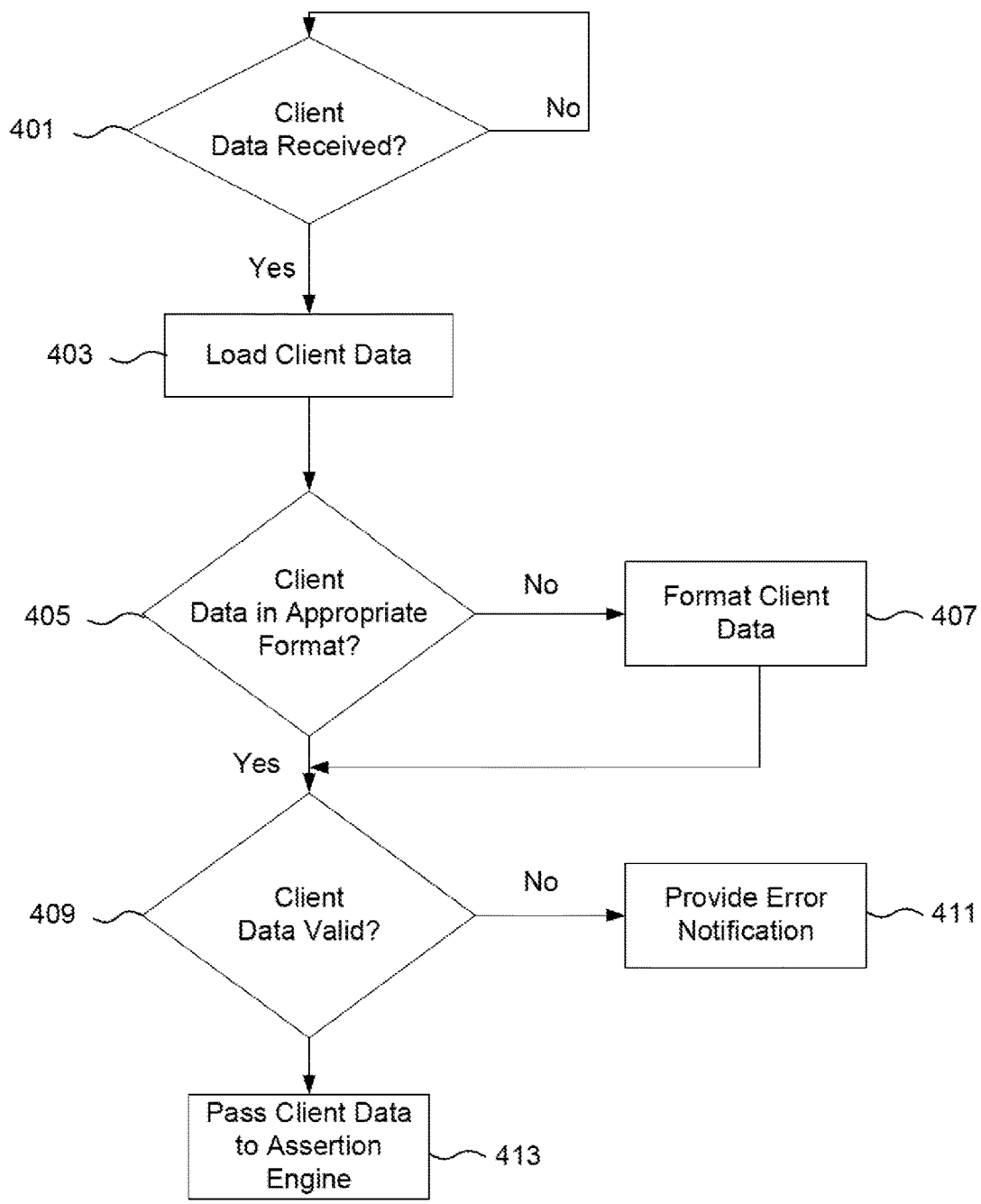
FIG. 4 is a flow diagram of loading and validating client data in accordance with aspects of the disclosure.

Referring now to FIG. 4, client data may be validated and formatted. For example, the server computing device 110 may receive client data, as shown in block 401. As previously discussed, the client data may be received from the storage device 150 or a coverage provider computer system 130. In the event the server computing device 110 fails to receive client data, the server computing device may continue to monitor for new client data. Upon receiving the client data, the client data may be loaded into the server computing device 110, as shown in block 403.

The loaded client data may then be formatted and/or validated. In this regard, each piece of client data may be analyzed to determine whether the data is in a format recognizable by the server computing device 110. For instance, the client data may be in XLS format, when a DOCX file is required. As such, the client data may be converted to XLS format. In some embodiments the client data may not be convertible to a recognizable format. As such, the server computing device 110 may provide a notification, such as a visual or audio alert, to a display notifying a user of the program that an error has occurred.

The client data may then be validated, as shown in block 409. For instance, one or more pieces of client data may be reviewed to check whether the value and/or text of the client data satisfies expected parameters. In this regard, one or more pieces of client data may be compared to baseline values or table entries. For example, revenue codes in the client data may be compared to a table of known revenue codes to assure the revenue codes in the client data are valid. In some embodiments the client data may not be valid and may be disregarded or segregated from the valid data. Additionally, the server computing device 110 may provide a notification, such as a visual or audio alert, to a display notifying a user of the program that an error has occurred, as shown in block 411. The validated data may then be passed to an assertion engine, as shown in block 413. Moreover, the client data may be augmented linked and/or augmented as described above.

Figure 5:
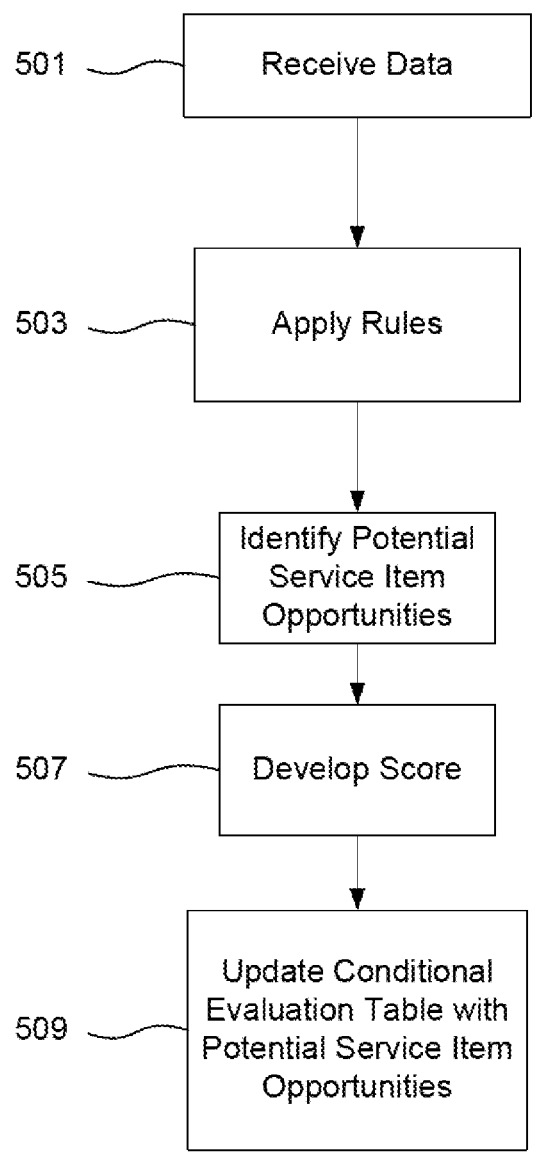
FIG. 5 is a flow diagram of applying an assertion engine in accordance with embodiments of the disclosure.

Referring now to FIG. 5, a process 500 for identifying service item management opportunities may be performed. In this regard, each piece of client data, including newly received data and/or previously processed data may be reviewed de novo. For example, as shown in block 501, for each client, the client's data, including previously processed client data, may be received at the assertion engine. For each piece and type of data (e.g., Lab Values, Prescribed Drugs, etc.) the assertion engine may apply rules to determine subsets of values associated with the rules and additional data, as shown in block 503. For instance, the assertion engine may apply one or more conditional rules (e.g., if/then/else conditional rule(s),) to the relevant data to identify potential service item management opportunities. In some embodiments statistical analysis and clinical judgment may be used to adjust the value (i.e., confidence) of the potential service item management opportunity. Sets of rules may be programmed to examine possibilities for conditions within a particular domain of data (e.g., drugs, lab results, medical equipment and supplies, etc.)

In one example, rules the client's data may indicate two lab results with "high" blood sugar findings over the last three months. Such a finding may merit an inference of diabetes Type II with low confidence (e.g., a 2 rating) because the client may not have fasted long enough, or there was an error in the testing process. In another example, a client's data may indicate the use of a drug which is primarily used for treating a certain illness. This finding may in turn be mapped to tens of thousands of NDC codes, and where relevant, to HCPC codes when the drug is billed as a medical claim. Such mappings may carry a confidence factor that contributes to the overall confidence rating for the condition via the Judgment Engine discussed herein. Where a drug or class may have multiple uses, official ("on-label") or by common use ("off-label"), there may be additional rules that confirm or rule-out the alternatives.

In another example, the client data may contain a prescribed drug. The assertion engine may have a rule which culls through a reference table or other such additional data to determine what conditions the prescribed drug may be used to treat. For instance, the client may be prescribed insulin and the assertion engine may cull through the reference table to determine the drug treats diabetes, a potential service item management opportunity, as shown in block 505. In some embodiments a satisfied rule may not result in a potential service item management opportunity being found.

A confidence rating may be assigned to potential service item management opportunity, as shown in block 507. The confidence rating may rank the likelihood that the condition contained in the potential service item management opportunity exists based on the client data from which the potential service item management opportunity was determined. In this regard, a single use drug may receive a higher confidence rating than a drug which may be used to treat multiple conditions. In some embodiments, the confidence rating may be a value on a scale, such as a confidence rating from 1-5. Scale-based confidence scoring within the Assertion Engine may be adjusted based on clinical judgment and available statistics.

In the event that a single piece of client data satisfies a rule, but fails to result in the identification of a potential service item management opportunity, the rule may be linked to additional rule(s) to identify a potential service item management opportunity. For example, if the piece of client data results in datum indicative of a drug having multiple uses, such as FDA approved and off-label uses, the other rules may be used to determine whether additional client data is available indicating for which use the drug is being used.

Upon successfully identifying and scoring a service item management opportunity, the assertion engine may update the conditional evaluation table with the new opportunity, each discrete rule that suggests the existence of the new opportunity, the source of the data, and the confidence score specific to each discrete rule. For example, the conditional evaluation table may be updated to record the identified service item management opportunity in association with the identifiers for the client, the source transaction (e.g., claim ID), the condition potentially detected, the confidence rating found, etc. In the event the client data contains multiple service item management opportunities, the assertion engine may update the conditional evaluation table with each opportunity.

Figure 6:
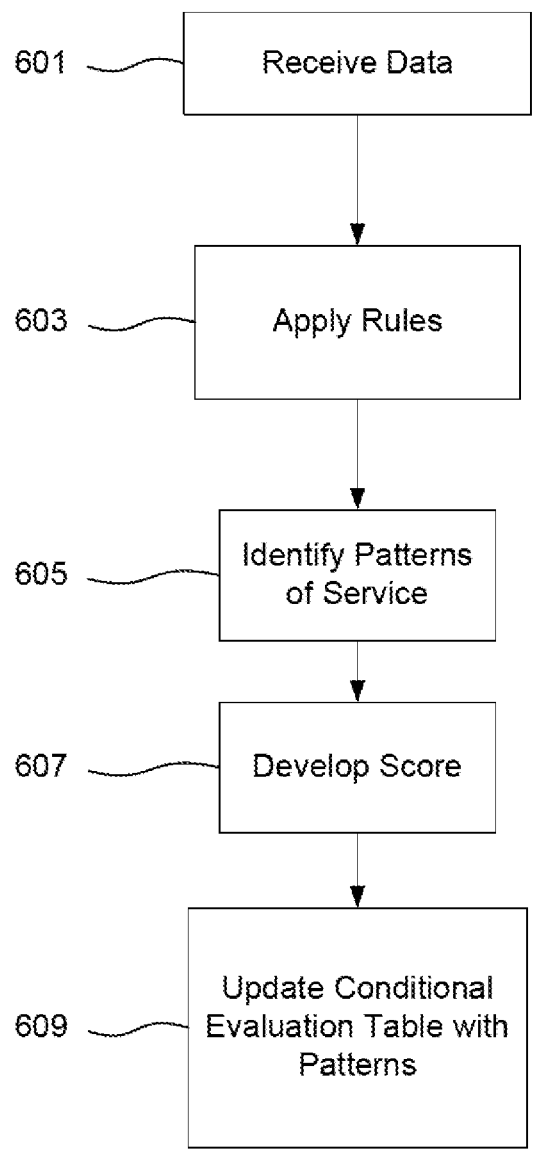
FIG. 6 is a flow diagram of applying an inference engine in accordance with aspects of the disclosure.

Referring now to FIG. 6, a process 600 may identify patterns of service based on the client data. For example, as shown in block 601, for each client, the client's data may be received at the inference engine. In contrast with the assertion engine, the inference engine may looks across data domains within an inference model, and may apply rules, such as multivariate scoring, that would be extremely cumbersome to render with conditional logic, such as complex interactions among multiple factors to determine patterns amongst the client data to identify service item management opportunities, as shown in block 603. For example, the client data may contain information regarding a newly prescribed drug and a number of lab tests. Based on this information the inference engine may determine a pattern indicating the client is being treated for a particular condition, as shown in block 605. This particular condition may be identified as a potential service item management opportunity.

For example, the inference engine may use condition predictive scoring, scoring from data mining, and/or combined identification and confidence scoring. Turning first to condition predictive scoring, for high-value sets of related conditions such as cancers or diabetes, techniques like logistic regression or discriminant analysis may be used that estimate the odds of a client having a particular condition or variant thereof (e.g., degree of control or complications of the client's diabetes or stage of cancer progression) as a function of several to many predictor variables. Each of the predictor variables may contribute a finite value or continuous value, which when summed across the variables yields a potential service item management opportunity along with an overall confidence score in the potential service item management opportunity.

Data mining scoring may include the use of advanced statistical techniques such as multivariate regression, survival models, neural networks, etc. to determine complex associations among many to dozens of variables within the client's data that predict the existence of a condition. For instance, data mining scoring might find that odds of having condition x are high among infants and geriatrics, but might be higher during adulthood for people with certain conditions, and the odds may further differ by gender, race/ethnicity, region of the US, etc.

Combined identification and confidence scoring may include the use of models such as Bayesian models which generate decision trees that discern among multiple service opportunities and the probabilities at each juncture of the client having the associated conditions. For instance, an article may state that someone who has a certain gene may have x times the odds of developing a condition or outcome. Some or all of the scoring variations may generate service item management opportunities and associated confidence probabilities.

A confidence rating may be assigned to a potential service item management opportunity found by the inference engine, as shown in block 607. In this regard, the inference engine may output both the condition(s) supported and the corresponding confidence values derived from the scoring model. The confidence factors output from the inference engine may be continuous across a range, such as 0-1, with zero meaning 0% confidence and 1 meaning 100% confidence. In the event the above discussed scoring variations fail to determine a score, the inference engine may analyze the distribution of output scores by clients in a validation data set and create a calculation that converts these scores into a standardized distribution. The scores may be normalized by excluding outliers and/or by transforming the overall distributions by taking the natural log, square root, or reciprocal of the raw score, yielding the needed probability scores.

Upon successfully identifying and applying a confidence rating to a service item management opportunity identified by the inference engine, the inference engine may update the conditional evaluation table with the new opportunity and related information. For example, the conditional evaluation table may be updated to record the identified service item management opportunity in association with the identifiers for the client, the source transaction (e.g., claim ID), the condition potentially detected, the confidence rating, etc. In the event the client data contains multiple service item management opportunities, the assertion engine may update the conditional evaluation table with each opportunity as well as additional discrete rule sets of supporting evidence for one or more opportunities.

Figure 7:
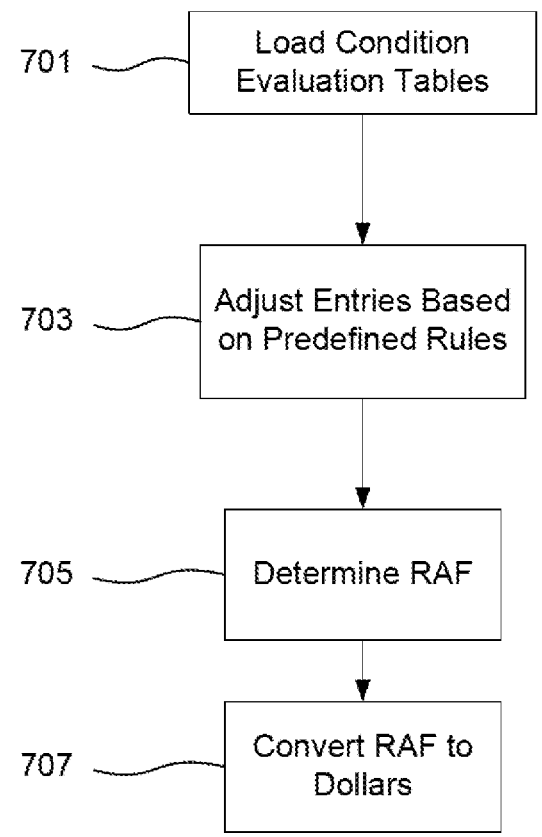
FIG. 7 is a flow diagram of applying a judgment engine in accordance with aspects of the disclosure.

A judgment engine may then access the conditional evaluation table to determine which service item management opportunities are actually occurring, and which previously identified opportunities have had key attributes change, as shown in block 701 of process 700 of FIG. 7. In this regard, multiple indicators of a particular service item management opportunity can arise coincidentally. However, more indicators do not necessarily imply that the particular service item management opportunity is more likely to exist. For example, service item management opportunities indicating two or more new starts in diabetic drug classes may indicate that a client actually suffers from diabetes. In contrast, doctors may try on several drugs on the client within a class until one is found that is best suited to the client and desired therapeutic outcome; whether they try one or four drugs in that class should not affect the confidence in this condition.

In order to determine which service item management opportunities are actually occurring for each client and which previously identified service item management opportunities have changed, the judgment engine may perform an evaluation using a number of rules, as shown in block 703. First, the current confidence value of a contributing item within a possible service item management opportunity may be adjusted upward or downward according to its age as well as the source of the client data (e.g., lab values, health assessments, etc.), strength of source, and other such variables. For instance, although older client data may be considered less predictive of a client's conditions than newer client data, the opposite may also be true. For example, certain conditions like multiple sclerosis enter dormant periods during which the client needs no active treatment, thus the data regarding the condition may be old, but still predictive of the client's conditions.

Another rule the judgment engine may determine is a composite strength for each service item management opportunity based on the respective service item management opportunities which represent a similar treatment. For example, a group of service item management opportunities identified through client data indicating multiple medications to treat the same condition may be grouped together. A composite strength may be assigned to the group of service item management opportunities by selecting the largest confidence value in the grouping of service item management opportunities, or another confidence value, and applying that confidence value as the composite strength. In other cases the presence of multiple similar medications may strengthen the inference, such that the composite strength will be greater than any individual service item in that group.

For each group of service item management opportunities identified by the assertion engine, the resulting adjusted confidence values may be consolidated and compared to a threshold value. When the consolidated value is greater than the threshold value, there is a probability that the service item management opportunity exists. For example, for service item management opportunities resulting from lab scores and medication scores, the service item with the highest adjusted confidence value may be added to the medication with the highest such score (or against a summary medication score where multiple treatments are additive), the highest procedure-related score, and so forth across all contributing data domains. This summed value may then be compared to a threshold value. There may be different threshold values for different types of conditions, which may be used to fine-tune the sensitivity vs specificity of the condition inferences.

The judgment engine may apply a rule which looks for duplicate conditions. In this regard, each identified service item management opportunity suggesting the same condition for a client, may be grouped and entered into the conditional evaluation table as a single entry. As the ratings and/or scores for the single entry are updated based on new data, the conditional evaluation table entry may also be updated.

The judgement engine may adjust the entries in the conditional evaluation table for hierarchies. In this regard, many of the condition classification systems used in healthcare use hierarchies for certain diseases and disorders. For example, the hierarchy for cancer may reflect the progression of the disease, such as stage 1 through stage 4 cancer, the existence of complications of the disease as it progresses, and complex situations like a diabetic also suffering congestive heart failure where the additional condition requires very different treatment from the other. The classification systems may account for these situations by defining hierarchies among them, allowing risk-adjustment for only the most severe condition supported. As such, the judgment engine may determine whether one of the entries in the conditional evaluation table is above another entry in the hierarchy. When this condition is present, the entry may be marked as being a more severe condition. The less severe entries may be removed or ignored. In the event entries belong to a grouping that is not hierarchical, the judgment engine may select the entry having the highest confidence score. Additionally, the judgment engine may identify the strongest entry (i.e., the entry with the highest score) for a condition and its year.

A risk adjustment factor (RAF) for service item management opportunities may be determined, as shown in block 705. The RAF may be determined by analyzing additional data, such as the client's specific type of benefit coverage, geography, age, gender, amount at which the client's premium is federally subsidized. Additionally, the judgment engine may analyze interaction among specific condition pairs, as the treatment of certain disease pairs may be costlier and more complex than the cost of treating each alone. Systems like HCCs offer added points in such situations. Additionally, the RAF may be determined by analyzing age-specific considerations.

For Medicare Advantage and the ACA, CMS develops and makes available HCC scoring software on their respective systems, such as servers. This software may take the additional data and calculate RAF points, such as RAF points attributable to the client's age/gender (i.e., the "demographic risk score"). For instance, the software may determine the sum of the RAF points (i.e., the "confirmed risk score" representing the total risk score based on the sum of the demographic risk score, confirmed condition score, and interactions/severity risk score) and additional RAF points for certain HCC combinations such as where the cost to care for conditions X and Y is greater than X+Y, (i.e., "interaction/severity risk score"). The software may also handle adjustments for other allowable factors (geographic factor, premium subsidy level, coverage level (e.g., bronze, gold, platinum, etc.), as well as the situations where the RAF for the conditions is shifted from the "confirmed risk score" to the "demographic" score.

The RAF may be converted to dollars based on the program being used by the client, as shown in block 707. As such, different methodologies may be used for relating risk-adjustment points to premiums or other sources of revenue. For instance, in Medicare Advantage, each plan may have insurance products and benefit plans by geographic unit for which CMS approves a Per Member Per Month (PMPM) premium whose submitted values are based on prior year's results and other underwriting factors, covering a plan year. For each service opportunity "verified" by CMS upon receipt of an acceptable claim or medical record supplemental submission, the incremental premium receivable becomes the bid rate for that client multiplied by the RAF points of that condition, plus any incremental premium for interaction/severity risk score (which is typically provided in points). Clients who are classified by CMS as "New Enrollees" are scored like ACA's infants with just a demographic score, and the difference may be calculated pre/post and the differential points times bid rate may be applied.

Medicare Advantage may be subject to a time-value of risk-adjustment. The time value of risk-adjustment means that the sooner the confirming transaction is approved by the CMS RAPS or EDPS server, the sooner the added premium becomes billable. During predetermined periods, CMS may consolidate the individual changes into product-level rollups. The product-level roll-ups may be used to premium lifts, against which actual figures may be compared.

ACA may be retrospective. In this regard, incremental RAF points may be amassed throughout the plan year, with an optional claim runout period of four months, or more or less, to allow for claims to adjudicate. CMS may allocate premiums based on a comparison of each plan's actual results against the results of the other plans. Plans with a client population who are more prone to illness ("sicker", as indicated by the RAF points, may receive incremental premiums from the other plans with a client population who is less prone to illness ("healthier"). Such a reallocation of premiums may level out premiums within the "sicker" and "healthier" populations. Therefore, plans cannot know with certainty whether they will receive or pay, much less how much.

To account for the uncertainty, market data, such as data from health insurance consultancies, may be used to model the market and to estimate the expected PMPM contribution to the Year-end Expected Transfer Payment. Based on these estimates the RAF may be converted to dollars. For instance, an estimate of a plan's end of year transfer payment at the state/Health Insurance Oversight System (HIOS)/market/coverage level may be made.

An ACA Risk Transfer Payment Modeler may estimate the monetary value of the RAF by determining how model inputs affect projected transfer receipts vs payments, and how to use these data to fine-tune the pricing and design of ones' ACA product line. In this regard, the Risk Transfer Payment Modeler may model competitors in each state, HIOS, market, coverage level, and on/off-exchange, to provide potential impacts of observed market behavior and/or of potential product/pricing changes in products offered.

The Risk Transfer Payment Modeler may recursively revise each model based on the models' output. For instance, a plan may know the total clients in a competitor's plan, but not exactly by market or coverage level, but may have market share estimates from previous models which may be used to populate the other values.

Reference adjusters, such as subscription services which supply estimates of plans' risk transfer payments, may be entered into regression models to generate a coverage provider's variance from the state averages. By varying a handful of such adjusters the coverage provider's may be provided with a reliable estimate of the degree to which they vary from their competition across these key metrics, which in turn enables them to fine-tune product design and pricing.

The Risk Transfer Payment modeler may estimate the monetary value of the RAF across levels of coverage in view of their competitors. In this regard a coverage provider may be provided with summaries of their competitors' products in view of their respective coverage levels. Further, for each competitor in each coverage level in each market, as well as in the summaries, the sensitivity of the results to variants of the estimated Plan Level Risk Score (PLRS, the result of risk-adjustment plus demographics) may be calculated as follows: the estimate itself along with +/−variants ranging from +/−1% to 30%, or more or less. The coverage provider may be provided with graphs of the results which provide insight into how slowly/quickly the profitability varies.

In addition to the ACA Risk Transfer Payment Modeler, an ACA Incremental Benefit calculator may be used to convert expected year-end risk transfer payments from the Risk Transfer Payment Modeler or reference adjusted into the dollar per RAF point multipliers. These multipliers may be used to monetize the contribution of each service item management opportunity which is closed.

Medicaid functions as an ACA/MA hybrid, where changes in prior plan years' risk scores due to risk adjustment "imply" a particular increase or decrease in premiums. However, like the ACA, most Medicaid programs cap individual plans' increases based on the total increase in the market's aggregate risk scores across all plans. In this regard, increases may be capped in two ways: rate of growth for the plan, based on a retroactive 2-year moving average, and also based on the plan's performance relative to its peers.

Based on the scored confidence of existence of the identified service item management opportunities, as well as the monetized value of the identified service item management opportunities (both with and without discounting for level of confidence), the client may make a determination whether or not to pursue one or more of the identified service item management opportunities. Such a determination to intervene and pursue an opportunity is to "close" a gap.

Interventions may include a number of activities taken to close gaps, such as linking the client with a health care provider so a condition may be diagnosed or properly documented, or b) reviewing independently the medical records of a client in hopes of finding the support needed to close the gap, but which had not previously been submitted in the measurement period.

A client may maximize a return on investment, by closing a gap only when the potential incremental benefit sufficiently exceeds the cost of the intervention (i.e., when closing the gap has a high return on investment (ROI)). For instance, an intervention where the gap is likely to close on its own (i.e., a "natural gap closure,") such as when a client who seeks care regularly of a health care provider who documents properly the condition's diagnostics and treatment and who is part of a practice that employs coders who ensure the chart is coded completely and accurately on claims submitted, is not a necessary intervention worth pursuit as the gap would have closed without any additional expense incurred by the coverage provider.

To determine the probabilities that a gap will close naturally within a targeted time period predictive modeling of a line of business that uses past behavior and other characteristics of the condition, client, and involved health care providers of the service item management opportunity. For example, for each opportunity a probability that a gap will close naturally may be determined by performing the following steps:

a. Quantify previous year's utilization, including visits to ER, inpatient, office, consultations;
b. Extract Coverage Providers opportunities for payment year (our master listing of open opportunities);
c. Extract at least 2 prior years of claims to measure gap closures;
d. Extract previous year financial data like allowed & paid amounts, member out-of-pocket;
e. Build categories from clusters of more detail, such as certain condition groupings;
f. Compute number of months since gap closed. The anchor year may vary by coverage provider and dependent on the volume of historic data. Value may be adjusted so the logistic regression model converges;
g. Create various categories (bins) from certain continuous variables;
h. Combine data;
i. Run logistic regression model and save output, predicted probabilities, etc;
j. Convert model results into scoring algorithm and apply to incoming data; and
k. Primary output=client/condition-specific closure odds.

Based on the closure odds, a coverage provider may decide to take steps to close the service item management opportunity or allow the opportunity to close naturally.

Coverage providers may have different objections and risk-tolerances for pursuing an opportunity. For instance, a coverage provider may have a fixed budget from which to maximize returns for intervention activities, along with the ability to forecast the incremental returns from additional investment. Another coverage provider may wish to achieve a minimum "lift" in RAF points, dollars, or quality gap closures regardless of cost.

To improve the determination of whether a service item management opportunity should be pursued, models within a Dynamic Intervention Planning module may be continually updated. Because each line of business (ACA, MA, Managed Medicaid) differ markedly in utilization, disease prevalence/incidence, utilization behavior, and more, Dynamic Planning Models are always developed specific to each sector. Because there is much regional variation in many of these factors, and different coverage providers manage their member and provider populations differently, Pulse8 builds a Dynamic Intervention Model specifically for each client/LOB combination that refreshes periodically to reflect the increasing number of member-years of data and most recent market changes; for largest coverage providers with millions of members this can occur as often as monthly. Each model within the Dynamic Intervention Planning module may provide recommendations on whether to pursue an intervention based on a coverage provider's preferences. These models may be continually updated in view of the following factors:

a. The odds for each identified service management opportunity closing naturally within the targeted plan year, based on relevant attributes for that specific client and for that particular condition;

b. Unless a coverage provider specifies otherwise, each service item management opportunity may be allocated to the type of intervention with best likelihood of closing the gap. In this regard, "surveillance" may be an option. Surveillance may include doing nothing until the gap closes naturally, or until sufficient data accumulate or enough time elapses to warrant intervention. This initial allocation acts as a "coarse filter" with minimal exclusions, and is used later to quantify the amount of intervention effort and resources that would have been wasted but for the Dynamic Intervention Planning.

c. Adjust the scoring of the client-condition opportunity to reflect the impact of the health care provider and associated group and entity (group of groups) on the odds of the gap closing. This increases the odds of closure if the health care provider documents thoroughly and her back-office staff (who supports all of the health care providers in that group or set of groups) abstracts comprehensively all the relevant diagnoses and codes precisely those conditions. Conversely those clients seeing health care providers who use preprinted forms of their most prevalent procedures and conditions, known as "super bills", which they seldom augment with additional or more precise codes, will therefore lower the odds of gap closure.

d. Non-activated recommendations are "recycled" into the next period's processing and evaluating, updating as data accumulates.

e. Results are compared with predictions to find improvements for the predictive models.

f. Direct ROIs are calculated from opportunities confirmed by performed interventions and not claims. Additional savings from eliminated waste and "free RAF" from gaps left to close naturally are calculated from contrasting results from the coarse and fine filtering steps.

The recommendations from the Dynamic Intervention Planning module may be presented to a coverage provider in the form of a chase listing which includes some or all of the recommended interventions. The coverage provider may filter the recommendations according to their objectives and risk-tolerance. Interventions may be selected to be acted upon are termed "activated interventions" and act as a "fine filter" that complements the original coarse one. These selected activated interventions may be transmitted to outside vendors for completion and the status of the intervention may be tracked throughout their respective life cycles based on regular status updates from each vendor.

Health care provider-focused interventions may include interventions where a health care provider is contacted to close a gap. There may be three types of health care provider-focused closures include prospective, concurrent, and retrospective. Prospective closures may identify for specific health care providers those clients who the health care provider's staff should either contact to make an appointment, or have available when the client visits the provider. The clients' respective PCP (Primary Care Practitioner), being the clients' gatekeeper and gateway to other health care providers, may typically receive alerts on all of a coverage provider's gaps, while specialists receive those for only the conditions that they typically diagnose or treat. Facilities typically receive all gaps as their medical record departments tend to be the most thorough at finding and documenting quality metrics and comorbidities and complications. Some coverage providers may bypass facilities for interventions.

Concurrent closures may include interventions when the targeted client next sees the health care provider. The health care provider may have available a checklist of specific gaps for which the client should be evaluated ("real-time Provider Alert"), as provided by the dynamic intervention planning module. These Provider Alerts can be directed to any health care provider.

Retrospective closures may identify health care providers, or the group that does the abstracting and coding of records and claims for groups of associated providers, who recently saw clients with outstanding gaps. The medical records from these recent visits may be reviewed to find diagnoses or other evidence of closure that were not previously documented in the claims. These reviews may be done on-site, remotely via secure linkages with the providers' EMRs, or via physical copies of those records.

Client-focused interventions may include interventions where a client is contacted to close a gap. For instance, a client may be contacted to seek a doctor's appointment ("Client Outreach") or to visit another convenient setting such as local pharmacies that staff, such as a nurse practitioner or physician assistant, who are allowed to diagnose certain conditions may see them.

Client-focused interventions may be initiated via communication channels such as a phone call, email, or mail. These communications may remind a client to visit their PCP or specialist for a baseline evaluation, visit their PCP for an annual wellness exam, that the client has an overdue or missed appointment, or provide an incentive to visit a local pharmacy or PCP.

In some embodiments client-focused interventions may include having a health care provider visit the client at their home or other location, providing a video or telephone call to assess a client, or providing a remote collection of telemetry that would substantiate a diagnosis made remotely (e.g., cardiac arrhythmias, sleep apnea, heart failure, diabetes).

In some embodiments an intervention may not be recommended. Rather, a wait and see approach (i.e., surveillance), may be recommended. In this regard, opportunities which are not "activated" may remain in the system and continually monitored. Based on a coverage provider's instructions, an opportunity may be watched and the coverage provider may be reminded of the opportunity at a later date. For each opportunity subjected to the wait and see approach a coverage provider may select to watch the opportunity, be reminded about the opportunity, escalate the opportunity, or cancel the opportunity.

Watching an opportunity may include doing nothing for one or more payment cycles. Such an approach may be recommended where a natural closure is expected or if a current PCP alert yields closure. Watching an opportunity may also be recommend for cases where the health care provider informs the Provider Feedback Loop that the client does indeed have this or similar diagnosis within this condition, so alerting for duration sufficient for a substantiating claim to arrive and adjudicate may be suspended. Reminding about an opportunity may include resending an alert to a PCP or specialist, or contacting a client via mail, email, or phone call. Escalating the opportunity may include scheduling an In-Home Assessment to an opportunity that formerly was a provider alert and cancelling an opportunity may include providing no further alerts for a condition of the client unless significant supporting data emerges later.

In order to match service item management opportunities with an intervention type an allocation manager may rebuild and/or refine at least annually an analytic model that selects an appropriate intervention type given time elapsed within Plan Year and other attributes of the opportunity gap, the coverage provider, and associated health care providers. In this regard, as part of each processing cycle, the Allocation Manager may scan all open opportunities that are not associated with an active intervention, and allots them to the intervention with the greatest odds of success. For example, the allocation manager may determine a client sees a PCP belonging to a group that shares performance risk with the health plan would qualify only for Provider Alerts. As risk-sharing arrangement places the onus of documentation on the health care providers, they are in the best position to determine on their own how best to close the gaps. The coverage provider's obligation in this case simply to tell the group who has known gaps.

In another example, the allocation manager may determine a client, during the current Plan Year has seen a facility, PCP, and/or specialist(s) which would qualify for Medical Record Review(s) for each client/gap/health care provider combination, as the specialist's area of practice would typically diagnose and/or treat the medical condition associated with the service item management opportunity being allocated. For instance, a cardiologist may only receive heart/circulatory opportunities, whereas an endocrinologist may see most every gap for a client as diabetes can manifest complications in many organ systems.

In yet another example, a client who has not seen a physician but who is suspected of high-value conditions (which would raise the coverage providers RAF), will be recommended for In Home Assessment, but may first be offered a telehealth consultation or free visit to a local pharmacy mini-clinic.

To assist in the management of the interventions, coverage providers may schedule specific types of interventions for specific times of the year. In this regard, the coverage providers may take a "campaign" approach to intervention management. In the campaign approach the system may generate a chase listing with all of the recommended interventions. The chase listing will not be reported to the coverage provider except at specific times of the year, the net effect being that during the off-months none of the opportunities are "activated", so they stay in the pool for the next processing cycle.

The Dynamic Intervention Planning module may generate an intervention-specific chase listing, such as an electronic workbook or other such document, that can be filtered and manipulated by the coverage provider in various ways to meet their specific needs for that particular type of intervention. The chase listing may be instantiated in most any format such as .xls or other database type format or may be accessed through a secure web application. The chase listings include columns of filterable and searchable attributes to maximize client's choices and to allow for a standard layout across coverage providers. In this regard, the chase listing may include attributes such as client-focused interventions, such as 1 row per family/household or per client and health care provider focused interventions, such as one per health care provider, specialist, etc.

The chase listing may include attributes for each subject area. For example, the chase listing workbook may include the following attributes: as follows:
 a. Client: identifiers, contact information, socio-demographics, coverage
 b. PCP: specialty, contact information
 c. Group Practice and/or "Entity" (group of related group practices such as an ACO), if any
 d. Special flags/counters: PCP Visits, PROVType (discerns PCP from facility from specialist)
 e. Predictive Models' Output: Chase Rank from factor analysis model, and Closure Probability Decile based on total rows in selection listing For each opportunity gap relevant to a particular household, client, and/or health care provider, the chase listing may include a sum, and store as separate columns its closure value (potential) in points and dollars (if derivable) from the following:
 a. Risk-adjustment: RAF and Financial Impact for:
  a. Unadjusted ("raw"). Sizes potential if confirmed and is typically most appropriate for individual estimations.
  b. Confidence-adjusted. Sizes expected value for the set of opportunities given expected closures.
 b. Quality gap closures: Points and dollars if available for
  a. The measure itself
  b. Improvement over time, if relevant
  c. Premium increase/(decrease), currently relevant for Medicare Advantage Stars quality program Return on investment estimates may also be included in the chase listing workbook. The return on investment estimates may depend on calculations at the following two levels:
 a. Global or model level: Parameters that affect all rows such as estimates of yield by low, expected, and high scenarios. Changes here may ripple through the entire dataset. This level also includes a template to summarize various "what if" modeling results, and tables of Expected Performance of each of the three scenarios (below), both direct ROI and additional benefits from Dynamic Planning:
  i. Clients touched
  ii. interventions targeted and expected completions, along with their cost including incentives
  iii. Expected yield rates for completed interventions
  iv. Global inflator/deflator factors, e.g., add or deduct an additional X percent to account for factors not quantified elsewhere
  v. Gross and net projected benefits and ROI resulting from the above factors applied to the client's data and derived data b. Dynamic Planning's additional benefits include
  i. Savings from interventions avoided=Total Chases−Chases Activated) x Cost per intervention
  ii. "Free RAF"=Sum of AdjustedRAF for chases that are
    a) in top deciles as most likely to close on own, and b) were excluded from Chases Activated for that reason Calculations may use data specific to each open opportunity such as the RAF and financial factors and often global parameters. For example, to determine the expected financial impact for an opportunity where this value is blank/zero, the AdjustedRAF for may be multiplied the average S/RAF derived from this dataset. If the calculation lacks global parameters, then the value changes only if the source data changes.

Once the source data have been modeled as described above, they are merged into a chase listing template. A return on investment estimation may also be included in the chase listing's summary The return on investment may be determined by the following:

A. Global parameters, such as those global or model level: parameters described herein.
B. Row-level parameters that apply the global parameters to the data in each row, apportioning costs of chases, and expected rates of completion and yield estimates across multiple interventions per member (such as Medical Record Reviews (MRRs)) so that the row contributions sum correctly across the dataset
C. Calculate row-level gross and net benefits, hence ROI and opportunity forgone (due to <100% yield).
D. Medical Record Reviews (MMRs) may contain two additional columns for client's convenience when manually filtering or aggregating the row-level data:
  i. Unique MemberID: set to '1' if first occurrence of unique ClientAltID, else '0'. Compare current row's value to one above it, '1' if differ, else '0'. Counting these yield distinct member counts.
  ii. Chase Counter: MRRs often target multiple providers because each takes a medical history and may diagnose conditions also diagnosed by other practitioners, as well as those only specialists like themselves could definitively detect. This column counts the number of providers who may be targeted for MRRs, and combined with provider-specific Chase Scores/Ranks, enables the coverage provider to determine the point of diminishing returns for additional chases for this member. Providers typically targeted include:
    1. PCP chase: all conditions that would be eligible for confirmation
    2. Facility Chases: all conditions
    3. Specialist Chases: only those conditions for which that specialty would typically diagnose or treat, based on table developed/maintained by clinicians.
E. Each chase listing may supplies three illustrative alternatives in a section called Option Summary Based on a blend of historical results, objectives of the coverage provider, time within the payment year, the Option Summary may presents an option with minimal filtering, filtering most appropriate for the coverage provider, and a more aggressively filtered alternative.
  i. The results may be laid out in a grid so that the coverage provider can contrast the relative impact of each option. More filtering (fewer cases chased) generally raises ROI but may reduce gross lift (returns). The grid includes counts of chases avoided, of members affected, gross and net returns, returns per completion, and more.
  ii. Each summary may include both ROI and its associated statistics calculated in the industry-standard manner, but also Dynamic Planning ROI with statistics for the additional benefits of savings from chases avoided, and (for prospective interventions) the estimated lift from opportunities allowed to close naturally. This DP ROI is reduced by the same completion and yield parameters as those pursued actively to be very conservative.
F. If coverage provider elects to receive the chase listing as a dataset or other type of file to manipulate on their premises, it is first encrypted before copying to sFTP server. Alert client to retrieve from this server to their sFTP server for decryption and use.

At this stage the coverage provider will retrieve and analyze the proposed Chase Listing, along with any recommendations presented. Based on the workbook, specific interventions to pursue or not may be made by the coverage provider. In this regard, the coverage provider may view the recommended interventions based on their previously determined intervention objective, such as to maximize RAF points regardless of cost, maximize likely ROI/RAF within a fixed budget, and/or optimize ROI/RAF regardless of budget.

The coverage provider may override as desired any global parameters, and may try various combinations and thresholds among the data columns to arrive at the desired tradeoff of opportunity costs and yields for selected opportunities to pursue. In order to determine which opportunities to activate the coverage provider may perform the following:

a. Pull/decrypt from sFTP site the Chase Listing workbook, or otherwise access the secure web application that accesses it behind one or more firewalls.
b. Review and adjust if needed, the model parameters
  i. Defaults: unit costs+incentives, data "plugs" like/RAF point
  ii. Yield, including expected rates of: completion, completions with incremental risk-adjustable confirmations
c. Review and adjust row-specific filters, notably but not limited to
  i. Threshold ROI, e.g., minimum low scenario ROI>n.nn
  ii. Closure deciles to exclude
d. Assess projected results, tweaking the above until satisfied with scenario
e. If multiple scenarios will be contrasted,
  i. Copy the output from this completed scenario into the supplied Options Comparison table, name it, and itemize the criteria used.
  ii. Repeat steps a through e.i for each remaining scenario
f. Determine the final criteria to finalize those interventions to be activated.

In one example a coverage provider may filter a chase listing workbook by removing the top 20%, or more or less, of listings which are estimated to most likely close on their own. The coverage provider may decide not to pursue these listings as they will likely close on their own and the coverage provider may realize savings from avoiding these chases. Further, the coverage provider may realize "free RAF" which allows the coverage provider to increase their risk adjustment factor without needing to chase any closures.

Continuing the above example, the coverage provider may also constrain the listings with estimated returns on investment greater than a threshold value, such as three times, or more or less. In the event a chase of the listing having an estimated ROI value greater than the threshold value is successful, the coverage provider will realize gains valued at three times, or more or less, that of the cost to chase the listing.

By filtering the chase listings, a coverage provider, or other user, may reduce the number of listings shown in a target list. As such, a user may be provided with a manageable amount of information to cull through. Moreover, the user may identify those listings which would be worthwhile to chase and see the estimated returns of those listings Once the coverage provider has decided on which interventions to pursue and which interventions to not pursue, they may upload the selections to the system, such as server 110. The selections may be marked as "activated," and those not selected may returned to the pool of opportunities to be re-evaluated in the next production data run. The chosen interventions may be packaged for the internal business unit or external vendor who will act on them. The package may be provided via the internet such as through encrypted sFTP in the form of an excel document with selections identified. In this regard, the chosen rows (indicating a chosen intervention) may be marked and those rows not selected may be deleted and/or moved to another tab. Alternatively the client may simply inform the system to via email what filter settings to use, so that the selections may be made automatically based on the filtered data.

Opportunities to be pursued may be i) formatted and forwarded to the appropriate entity to perform the requested type of intervention; ii) bypassed in future analytic runs except to close them upon receipt of acceptable confirming data, or for termination of the client's coverage; and/or iii) accompanied in the database by the intervention's key attributes: closure decile, estimated yield, Chase Score and Rank, other output from scoring/modeling as described previously. Those opportunities which are not activated may be re-evaluated during the next analytics run, updating their attributes as additional data accumulate.

The formatted opportunities may be compiled into a subset of only those intervention-specific attributes that the vendors need to close an opportunity. In this regard, the opportunities may include identifiers of the clients and health care providers, along with basic descriptors like contact information and client socio-demographics. Additionally, other fields such as vendor-requested fields like health care provider/group identifiers may also be included. The conditions being targeted may not be provided to the vendor to avoid the vendor from having an incentive to "find" a diagnosis that is not supported sufficiently by the chart. The formatted opportunities may be shared via encrypted files.

As vendors proceed with working through an intervention, coverage providers may choose to receive notifications on the status of the intervention. In some embodiments coverage providers may select no intervention management. For coverage providers who choose to receive notifications on the status of their selected interventions, the coverage providers may be provided with a dashboard which shows the status of their respective interventions. In this regard, the system may manage the vendors on the coverage provider's behalf, actively assisting in selecting opportunities to activate, expediting and resolving bottlenecks, and/or ensuring quality of vendors' work. The system may update the dashboard to show the status of the interventions in real time, hourly, daily, etc.

Coverage providers may manage their own vendors and supply the updates to the system. The dashboard may be updated to track the status of the intervention process based on the updates supplied by the coverage provider.

For coverage providers who choose not to receive the status of interventions as they move through their respective life cycles, the dashboards may not be populated and/or not supplied. As such, the coverage provider would be responsible for tracking and managing their vendors as they work through interventions.

In order to determine the impact of a coverage provider's selected interventions, the effectiveness of gap closure efforts, specifically return on investment (ROI) may be determined. In this regard, the calculations and metrics reported may include the following:

a. Costs=Total expenditures made related to the type of intervention over the measurement period=Interventions activated times average fully loaded cost per intervention (defined below)
b. Benefits=Dollar value of "successful" interventions plus other benefits (both defined below)
   a. "Success"=intervention resulting in either
      i. Closing an opportunity still open as of the relevant cutoff date (defined below)
      ii. Documenting sufficiently a NEW opportunity not previously identified. That is, a false-negative opportunity.
   b. "Lift"=incremental RAF points from the success that is adjusted for
      i. Hierarchy/group: If 2 or more conditions within same group/hierarchy are "successes", then can only take credit for 1–the more severe condition
      ii. Interaction points: With some sets of HCCs the total RAF points allowed=the sum of the condition-specific RAF plus additional points that reflect the added complexity hence cost resulting from this combination.
c. Benefits=sum of RAF lift times the corresponding/RAF multiplier (defined below)
   i. Costs of interventions, including any health care provider incentives, education and other outreach
   ii. Net benefit=Total Benefits minus Total Costs
   iii. ROI=Total Benefits divided by Total Costs There may be multiple types of lift (i.e., incremental benefits) which can be used in the above calculations. The types of lift may include a direct lift where it has been confirmed conditions were previously open and indirect lifts for non-specific interventions like health care provider alerts where there is often months lag between the alert and the confirming event. Indirect lift may be estimated through a statistical model that contrasts the before/after risk scores of clients associated with the health care providers or region who received alerts with the before/after scores of clients in same groups for whom no alerts were generated. The model may also control for natural gap closures. In this regard, when determining costs and benefits natural closures may not be considered intervention successes. Moreover, claims whose date of service precedes an intervention may supersede conditions also confirmed by the intervention, and may not count as an intervention success.

The RAF lifts may be monetized by Line of Business (LOB) as described herein, such as for the ACA, MA, and MC. The RAF lifts may also be monetized for risk-sharing coverage providers such as Accountable Care Organizations. Calculations may be tailored, for a price, according to the risk-sharing contract(s) which may be used in MA.

Benefits derived from the Dynamic Intervention Planning module may include savings from avoided chases (i.e., potential interventions identified by the Chase Listings minus activations, times the average cost per chase for intervention type,) and "Free RAF" points (i.e., RAF hence dollar lift for interventions not activated but along that were among the top deciles in likelihood to close naturally.)

In some embodiments, service item management opportunities may be assessed to determine whether the opportunity will pass the edits of the official CMS servers, such as EDGE for ACA and RAPS/EDPS for MA. In this regard, service item management opportunities may be confirmed for intervention.

Every potential service item management opportunity, whether or not identified in a prior run, is evaluated de novo each processing cycle, incorporating the latest information. Such data may include return files from CMS' official servers (EDGE for Affordable Care Act, RAPS and EDPS for Medicare Advantage), files from coverage providers' intervention vendors that itemize the diagnosis codes substantiated to their satisfaction ("coding files"), claims from prospective intervention vendors that include the diagnoses substantiated to their satisfaction during the exam in the home (IHA), health fair, workplace exams (often using a fully equipped medical office on wheels), pharmacy clinic, telehealth encounter, or other permitted settings or means. If a coverage provider has terminated coverage, previously open opportunities will remain for potential retrospective intervention, but may not qualify for any concurrent or prospective activity. Confidence levels routinely change as new data solidify support or contradict prior hypothesis. The opportunities, therefore, are part of a continuous feedback learning loop.

Opportunities that did not meet any criteria for selection for a potential type of intervention, along with those presented as "chase candidates" but which were not selected by the coverage provider for active pursuit ("activation") remain in the pool of open opportunity gaps. Changes in the client's or opportunity's attributes may suffice in a subsequent cycle to include as a possible chase. Intervention campaigns scheduled for later in the plan year will include opportunities hitherto bypassed by the other intervention types.

The Assertion Rules, Inference models, Predictive models, and other algorithms may be reviewed and/or recalibrated at least annually, or more or less. Further, the review and/or recalibration of the Assertion Rules, Inference models, Predictive models, and other algorithms may beperformed independently by line of business, to take advantage of additional data, reflect changes in medical practice or clinical reasoning. For Managed Medicaid where different states use different clinical grouping models (CDPS, CRGs, ACGs, ERGs), the results of each grouping technique are analyzed independently and in contrast to each other to detect inference associations that other techniques miss. More specialized analytics now probe more subtle inferencing logic and models, including reduction of confidence as a function of time (conceptually akin to a decay curve), conditions that recur sporadically such as certain cancers and MS. Conditions with lower yields are assessed with Machine Learning (e.g., neural networks) techniques to detect associations not easily found using classical parametric and non-parametric methods. These statistical mining and models may augment and supplant older, expert-driven rules in the Assertion Engine.

Most of the foregoing alternative examples are not mutually exclusive, but may be implemented in various combinations to achieve unique advantages. As these and other variations and combinations of the features discussed above may be utilized without departing from the subject matter defined by the claims, the foregoing description of the embodiments should be taken by way of illustration rather than by way of limitation of the subject matter defined by the claims. As an example, the preceding operations do not have to be performed in the precise order described above. Rather, various steps can be handled in a different order, such as reversed, or simultaneously. Steps can also be omitted unless otherwise stated. In addition, the provision of the examples described herein, as well as clauses phrased as "such as," "including" and the like, should not be interpreted as limiting the subject matter of the claims to the specific examples; rather, the examples are intended to illustrate only one of many possible embodiments. Further, the same reference numbers in different drawings may identify the same or similar elements.

The invention claimed is:

1. A computer implemented method for determining service item management opportunities, the method comprising:

receiving, at one or more processors, via a communication network, a set of client data;

determining, by the one or more processors, service items in the set of client data which satisfy one or more rules;

identifying one or more service item management opportunities for a coverage provider from the determined service items, the one or more service item management opportunities each representing a potential health condition of a client which was previously unknown or not entered into the set of client data;

identifying, by the one or more processors, one or more particular conditions by analyzing patterns of service based on the client data across data domains within an inference model using multivariate analysis;

assigning, by the one or more processors, a confidence rating to each of the one or more particular conditions;

identifying, by a judgment engine executing on the one or more processors, one or more additional service item management opportunities for each of the one or more particular conditions based on (i) the confidence rating of the particular condition, (ii) age of the client data, and (iii) a composite strength based on the client data indicating multiple medications prescribed to treat the particular condition;

assigning a confidence value, by the one or more processors, to the one or more service item management opportunities and the one or more additional service item management opportunities;

determining, by the one or more processors, for each of the one or more service item management opportunities and the one or more additional service management opportunities, a recommended intervention type based on the respective assigned confidence value; and causing, for each of the one or more service item management opportunities and the one or more additional service management opportunities, by the one or more processors, transmission, via the communication network to an external device, of rendering information indicating the service item management opportunity, the one or more additional service management opportunities, and the recommended intervention type.

2. The computer implemented method of claim 1 wherein identifying the one or more service item management opportunities further includes:

identifying, for each service item in the set of client data, a set of rules from the one or more rules;

determining for each service item, at least one validation test, based on the respective set of one or more rules; and performing, for each service item, each respective determined validation test to determine whether the service item satisfies at least one of the set of rules.

3. The computer implemented method of claim 2 wherein assigning the confidence value to the one or more service item management opportunities further includes:

for each service item in the set of client data determining a classification;

identifying a related service item from the set of client data based on the classification; and increasing the confidence value for a given service item management opportunity corresponding to a given each service item based on a given identified related item.

4. The computer implemented method of claim 1 wherein each of the one or more service item management opportunities are assigned a risk adjustment factor (RAF), and wherein the risk adjustment factor represents an opportunity score corresponding to a condition in which the one or more service item management opportunity is confirmed.

5. The computer implemented method of claim 4 wherein the RAF is normalized.

6. The computer implemented method of claim 1 wherein the transmission causes a visual or audio alert to be automatically generated at the external device.

7. The computer implemented method of claim 1 wherein the recommended intervention type includes one or more of surveillance, no intervention, a health care provider-focused intervention, or a client-focused intervention.

8. A system for determining service item management opportunities comprising:

an application server having one or more processors coupled to memory, the one or more processors being configured to:

receive a set of client data;

determine service items in the set of client data which satisfy one or more rules;

identify one or more service item management opportunities for a coverage provider from the determined service items, the one or more service item management opportunities each representing a potential health condition of a client which was previously unknown or not entered into the set of client data;

identify one or more particular conditions by analyzing patterns of service based on the client data across data domains within an inference model using multivariate analysis;

assign a confidence rating to each of the one or more particular conditions;

identify, using a judgment engine, one or more additional service item management opportunities for each of the one or more particular conditions based on (i) the confidence rating of the particular condition, (ii) age of the client data, and (iii) a composite strength based on the client data indicating multiple medications prescribed to treat the particular condition;

assign a confidence value to the one or more service item management opportunities and the one or more additional service item management opportunities;

determine, for each of the one or more service item management opportunities and the one or more additional service management opportunities, a recommended intervention type based on the respective assigned confidence value; and cause, for each of the one or more service item management opportunities and the one or more additional service management opportunities, transmission, via the communication network to an external device, of rendering information indicating the service item management opportunity, the one or more additional service management opportunities, and the recommended intervention type.

9. The system of claim 8 wherein identifying the one or more service item management opportunities further includes:

identifying, for each service item in the set of client data, a set of rules from the one or more rules;

determining for each service item, at least one validation test, based on the respective set of one or more rules; and performing, for each service item, each respective determined validation test to determine whether the service item satisfies at least one of the set of rules.

10. The system of claim 9 wherein assigning the confidence value to the one or more service item management opportunities further includes:

for each service item in the set of client data determining a classification;

identifying a related service item from the set of client data based on the classification; and increasing the confidence value for a given service item management opportunity corresponding to a given each service item based on a given identified related item.

11. The system of claim 8 wherein each of the one or more service item management opportunities are assigned a risk adjustment factor (RAF), and wherein the risk adjustment factor represents an opportunity score corresponding to a condition in which the one or more service item management opportunity is confirmed.

12. The system of claim 11 wherein the RAF is normalized.

13. The system of claim 8 wherein the transmission causes a visual or audio alert to be automatically generated at the external device.

14. The system of claim 8 wherein the recommended intervention type includes one or more of surveillance, no intervention, a health care provider-focused intervention, or a client-focused intervention.

15. A non-transitory computer-readable medium storing instructions, which when executed by one or more processors, cause the one or more processors to:

receive a set of client data;

determine service items in the set of client data which satisfy one or more rules;

identify one or more service item management opportunities for a coverage provider from the determined service items, the one or more service item management opportunities each representing a potential health condition of a client which was previously unknown or not entered into the set of client data;

identify one or more particular conditions by analyzing patterns of service based on the client data across data domains within an inference model using multivariate analysis;

assign a confidence rating to each of the one or more particular conditions;

identify, using a judgment engine, one or more additional service item management opportunities for each of the one or more particular conditions based on (i) the confidence rating of the particular condition, (ii) age of the client data, and (iii) a composite strength based on the client data indicating multiple medications prescribed to treat the particular condition assign a confidence value to the one or more service item management opportunities and the one or more additional service item management opportunities;

determine, for each of the one or more service item management opportunities and the one or more additional service item management opportunities, a recommended intervention type based on the respective assigned confidence value; and cause, for each of the one or more service item management opportunities and the one or more additional service item management opportunities, transmission, via the communication network to an external device, of rendering information indicating the service item management opportunity, the one or more additional service item management opportunities, and the recommended intervention type.

16. The non-transitory computer-readable medium of claim 15 wherein identifying the one or more service item management opportunities further includes:

identifying, for each service item in the set of client data, a set of rules from the one or more rules;

determining for each service item, at least one validation test, based on the respective set of one or more rules; and performing, for each service item, each respective determined validation test to determine whether the service item satisfies at least one of the set of rules.

17. The non-transitory computer-readable medium of claim 16 wherein assigning the confidence value to the one or more service item management opportunities further includes:

for each service item in the set of client data determining a classification;

identifying a related service item from the set of client data based on the classification; and increasing the confidence value for a given service item management opportunity corresponding to a given each service item based on a given identified related item.

18. The non-transitory computer-readable medium of claim 15 wherein each of the one or more service item management opportunities are assigned a risk adjustment factor (RAF), and wherein the risk adjustment factor represents an opportunity score corresponding to a condition in which the one or more service item management opportunity is confirmed.

19. The system of claim 18 wherein the RAF is normalized.

20. The system of claim 15 wherein the transmission causes a visual or audio alert to be automatically generated at the external device.

* * * * *